(12) United States Patent
Orbay et al.

(10) Patent No.: US 8,900,239 B2
(45) Date of Patent: Dec. 2, 2014

(54) INTERNAL JOINT STABILIZER FOR A MULTI-AXIS JOINT, SUCH AS A CARPO-METACARPAL JOINT OR THE LIKE, AND METHOD OF USE

(75) Inventors: Jorge L. Orbay, Miami, FL (US);
Thomas H. Norman, Miami, FL (US);
William Garcia De Quevedo, Miami, FL (US); Ronald Litke, Shelton, CT (US)

(73) Assignee: Skeletal Dynamics, LLC., Miami, FL (US)

( * ) Notice: Subject to any disclaimer, the term of this patent is extended or adjusted under 35 U.S.C. 154(b) by 906 days.

(21) Appl. No.: 12/904,646

(22) Filed: Oct. 14, 2010

(65) Prior Publication Data

US 2011/0087297 A1    Apr. 14, 2011

Related U.S. Application Data

(60) Provisional application No. 61/251,563, filed on Oct. 14, 2009, provisional application No. 61/347,517, filed on May 24, 2010, provisional application No. 61/390,420, filed on Oct. 6, 2010.

(51) Int. Cl.
| | |
|---|---|
| *A61F 2/46* | (2006.01) |
| *A61F 2/42* | (2006.01) |
| *A61B 17/68* | (2006.01) |
| *A61B 17/56* | (2006.01) |
| *A61F 2/30* | (2006.01) |
| *A61B 17/84* | (2006.01) |
| *A61B 17/86* | (2006.01) |

(52) U.S. Cl.
CPC ........... *A61B 17/68* (2013.01); *A61B 2017/567* (2013.01); *A61F 2002/30301* (2013.01); *A61F 2230/0095* (2013.01); *A61F 2002/4258* (2013.01); *A61F 2002/30772* (2013.01); *A61B 17/846* (2013.01); *A61F 2/4241* (2013.01); *A61B 17/86* (2013.01); *A61F 2002/30878* (2013.01)
USPC ..................................... 606/86 R; 623/21.15

(58) Field of Classification Search
CPC .............. A61F 2/42; A61F 2002/4253; A61F 2002/4258; A61F 2002/4276; A61F 2002/4279
USPC ......... 606/246, 263; 623/21.11, 21.12, 21.15, 623/21.16, 21.17
See application file for complete search history.

(56) References Cited

U.S. PATENT DOCUMENTS

| | | | |
|---|---|---|---|
| 4,054,955 A | 10/1977 | Seppo | |
| 4,276,660 A * | 7/1981 | Laure | ......................... 623/21.16 |
| 5,480,447 A * | 1/1996 | Skiba | ......................... 623/21.19 |

(Continued)

FOREIGN PATENT DOCUMENTS

| | | |
|---|---|---|
| DE | 102004019196 A1 | 11/2004 |
| GB | 2250919 A | 6/1992 |
| WO | 03005914 A1 | 1/2003 |

OTHER PUBLICATIONS

International Search Report dated Apr. 22, 2011.

*Primary Examiner* — Anu Ramana
(74) *Attorney, Agent, or Firm* — Laurence A. Greenberg; Werner H. Stemer; Ralph E. Locher (57) ABSTRACT

An internal device is provided for stabilizing a joint having multiple axes of rotation. The device includes two axles, separated by a body portion. The two axles are maintained by the body portion in a geometric relationship that replicates the geometric relationship of the rotational axes of the joint. The axles are installed into the bones of the joint to stabilize the joint.

7 Claims, 8 Drawing Sheets

(56) References Cited

U.S. PATENT DOCUMENTS

| | | |
|---|---|---|
| 5,549,690 A | 8/1996 | Hollister et al. |
| 5,645,605 A | 7/1997 | Klawitter |
| 6,159,247 A | 12/2000 | Klawitter |
| 7,837,739 B2 * | 11/2010 | Ogilvie ................ 623/21.15 |
| 7,976,580 B2 * | 7/2011 | Berger ................ 623/21.13 |
| 2004/0193279 A1 | 9/2004 | Roger |
| 2010/0063549 A1 | 3/2010 | Orbay et al. |
| 2010/0222820 A1 * | 9/2010 | Trieu ................ 606/255 |

\* cited by examiner

INTERNAL JOINT STABILIZER FOR A MULTI-AXIS JOINT, SUCH AS A CARPO-METACARPAL JOINT OR THE LIKE, AND METHOD OF USE

CROSS REFERENCE TO RELATED APPLICATION

The present application claims priority to: Provisional Patent Application No. 61/251,563, filed on Oct. 14, 2009, and entitled "INTERNAL JOINT STABILIZER FOR A MULTI-AXIS JOINT, SUCH AS A CARPO-METACARPAL JOINT OR THE LIKE, AND METHOD OF USE"; Provisional Patent Application No. 61/347,517 filed on May 24, 2010 and entitled "DEVICES, IMPLEMENTS AND METHODS FOR THE TREATMENT OF A MULTI-AXIAL JOINT" and Provisional Patent Application No. 61/390,420 filed on Oct. 6, 2010 and entitled "DEVICES, IMPLEMENTS AND METHODS FOR THE TREATMENT OF A MULTI-AXIAL JOINT", those applications being incorporated herein, by reference, in their entireties.

FIELD OF INVENTION

The invention relates to the stabilization of joints and the early reestablishment of adequate range of motion at the joints, and more particularly, to joint stabilization for the carpometacarpal joint and other similarly configured joints.

In particular, the carpometacarpal joint found at the base of the thumb is complicated in that it does not have a single axis of rotation. Rather, the first metacarpal sits on the trapezium in a kind of saddle shaped geometry. This allows the bones to rotate around distinct axes that are in a transverse orientation to one another.

DESCRIPTION OF THE RELATED ART

Dislocation and subluxation of joints are serious clinical problems that, if persistent, recurrent or chronic, can result in irreversible damage. These chronic instabilities are usually the result of damage to the supporting joint ligaments and/or the result of loss of bone integrity. Treatment of these conditions includes restoration of the proper relationships or "reduction" of the bones involved. Reduction must be maintained for a period of time sufficient to allow for healing of the damaged tissues. However, it is desirable to maintain joint motion during this period in order to prevent ankylosis and to maintain a healthy articular cartilage. Thus, the ideal immobilization for an unstable, dislocated or subluxed joint would prevent abnormal translational movements, but would allow motion similar to the joint's normal kinematics.

Internal joint stabilizers for the treatment of joint instability are known in the art. United States patent publication US2010/0063549 discloses stabilization devices for the elbow and for the interphalangeal (PIP) joints of the hand. However, known devices address the stabilization of joints having a single axis of rotation and are not suitable for joints having more than one axis of rotation.

BRIEF SUMMARY OF THE INVENTION

It is accordingly an object of this invention to provide an internal joint stabilizer which overcomes the limitations of the heretofore-known devices. In particular, a multi-axis, internal joint stabilizer is provided for stabilization of a carpo-metacarpal joint and/or similar joints having more than one axis of rotation.

Although the invention is illustrated and described herein as embodied in an Internal Joint Stabilizer for a Multi-Axis Joint, such as the Carpo-Metacarpal Joint or the Like, and a Method of Use, it is nevertheless not intended to be limited to only the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DETAILED DESCRIPTION OF THE PREFERRED EMBODIMENTS

Referring now to FIGS. 1A-3C, there is shown one particular embodiment of an internal joint stabilizer (IJS) 300 for a joint with multiple axes of rotation, such as the carpometacarpal (CMC) joint and similar. The IJS 300 includes two axle portions 310, 320 intended to be implanted into two bones 100, 200 of a joint, in alignment with two respective axes of rotation M, T of the joint. The two axle portions 310, 320 of the IJS 300 are joined together by a body portion 330 that keeps the two axle portions 310, 320 in the correct alignment relative to one another, which alignment is generally transverse to one another. In the particular case of the CMC joint, the two bones are the first metacarpal 200 and the trapezium 100.

Although described in the present embodiment as a single part device, the IJS 300 for a multi-axis joint could also be implemented as a multi-part device, such as the multipart device 400 of FIGS. 4A-4D, if desired.

Figure 1A:
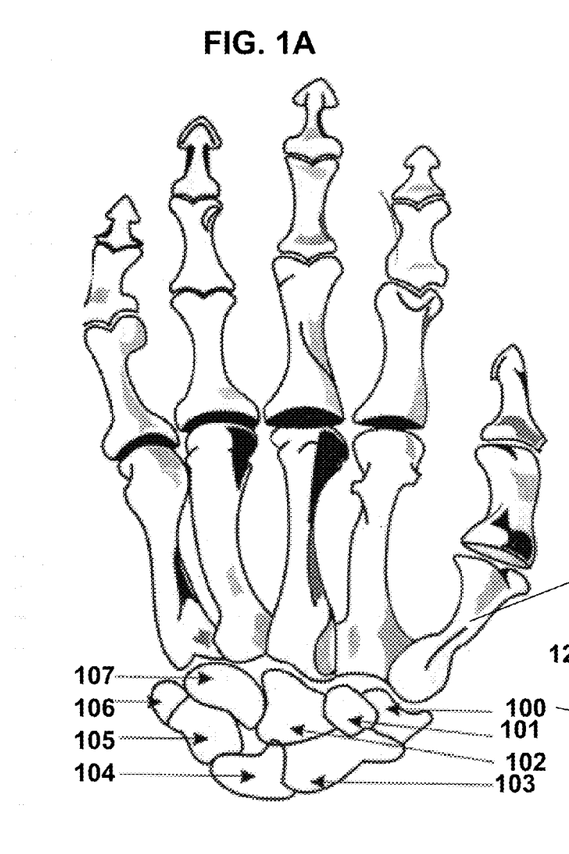
FIG. 1A is a diagrammatic view of the skeleton of the hand where the bones of the carpus and the first metacarpal are indicated.

Referring more particularly to FIG. 1A, there is shown a skeletal representation of the human hand and, in particular, the bones of the carpus and the CMC joint; the trapezium 100, the trapezoid 101, the capitate 102, the scaphoid 103, the lunate 104, the triquetral 105, the pisiform 106, the hamate 107 and the first metacarpal 200. Together, the first metacarpal 200 and trapezium 100 form the CMC joint at the base of the thumb.

Figure 1B:
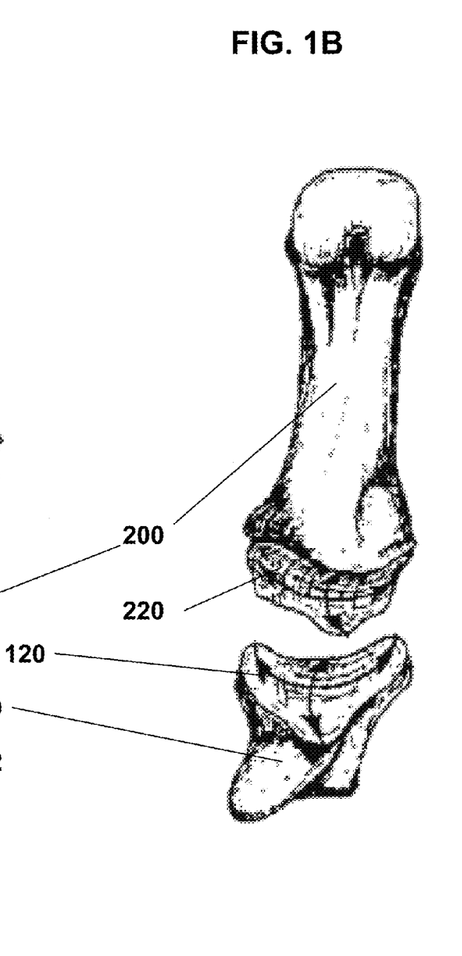
FIG. 1B is an exploded view of the bones that compose the carpometacarpal joint.
Figure 2A:
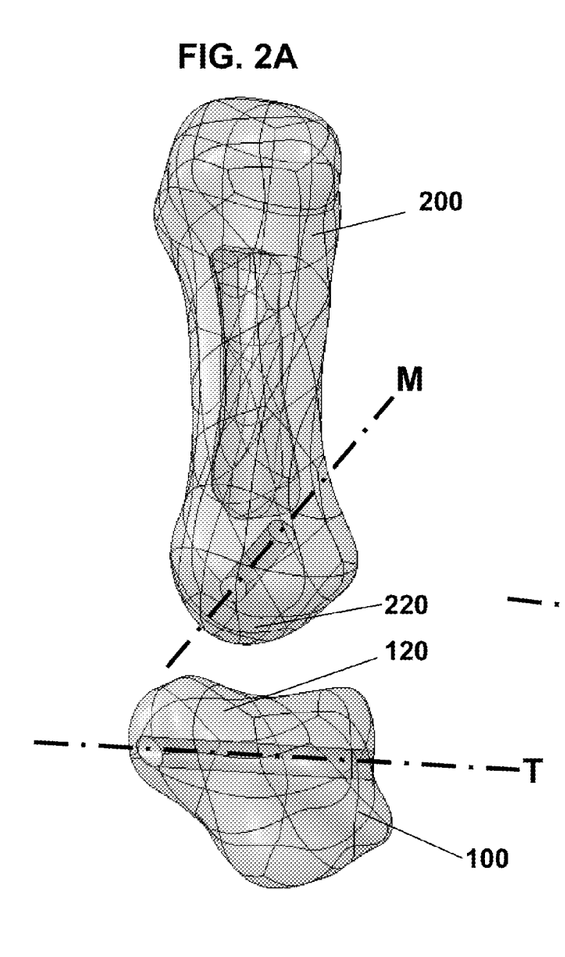
FIG. 2A is an exploded view of the bones that compose the carpometacarpal joint indicating the two saddle shaped articular surfaces and the two axes of rotation.
Figure 2B:
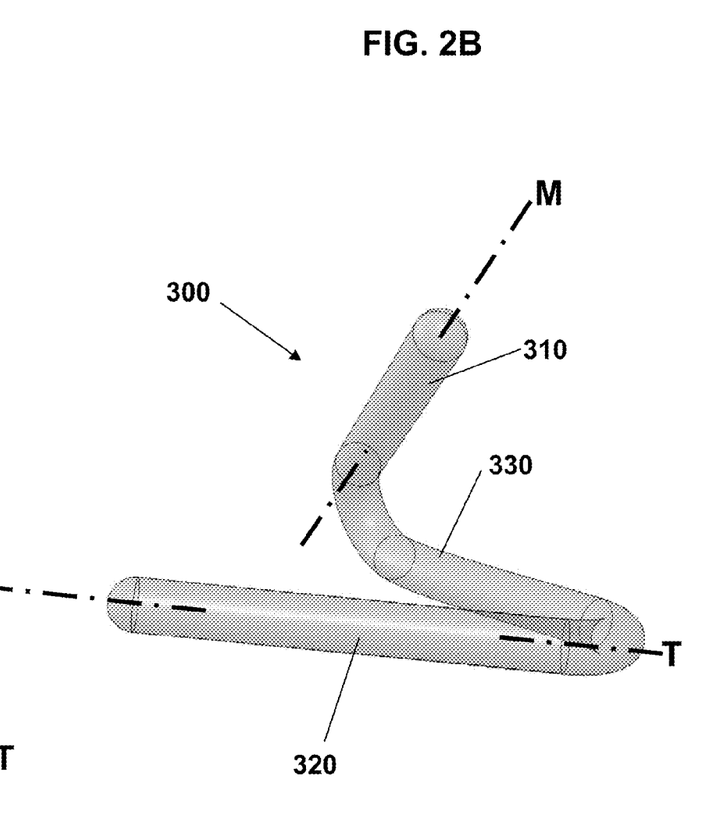
FIG. 2B is an enlarged perspective view of a single part internal joint stabilizer in accordance with one particular embodiment of the invention.

FIGS. 1B and 2A show the CMC joint, formed from an interaction between the first metacarpal 200 and trapezium 100, slightly separated to exhibit the saddle-shaped characteristics of the articular surfaces 220, 120 of the first metacarpal 200 and the trapezium 100, respectively. Such articular surfaces are typical of joints having more than one axis of rotation. As shown more particularly in FIG. 2A, the CMC joint has a first axis of rotation M defined through the first metacarpal and a second axis of rotation T defined through the trapezium.

Referring now to FIG. 2B-3C, there is shown one particular embodiment of a single part IJS 300 for the CMC joint. The IJS 300 has a first axle portion 310 adapted to be installed in the first metacarpal 200 in alignment with the first axis of rotation M and a second axle 320 adapted to be installed in the trapezium 100 in alignment with the second axis of rotation T. The first axle portion 310 and the second axle portion 320 are joined by a body portion 330. The geometry of the body portion 330 is adapted to join the two axle portions 310, 320 in a spatial relationship that replicates the spatial relationship between the first axis M and the second axis T of the CMC joint.

Figures 3A, 3B, 3C:
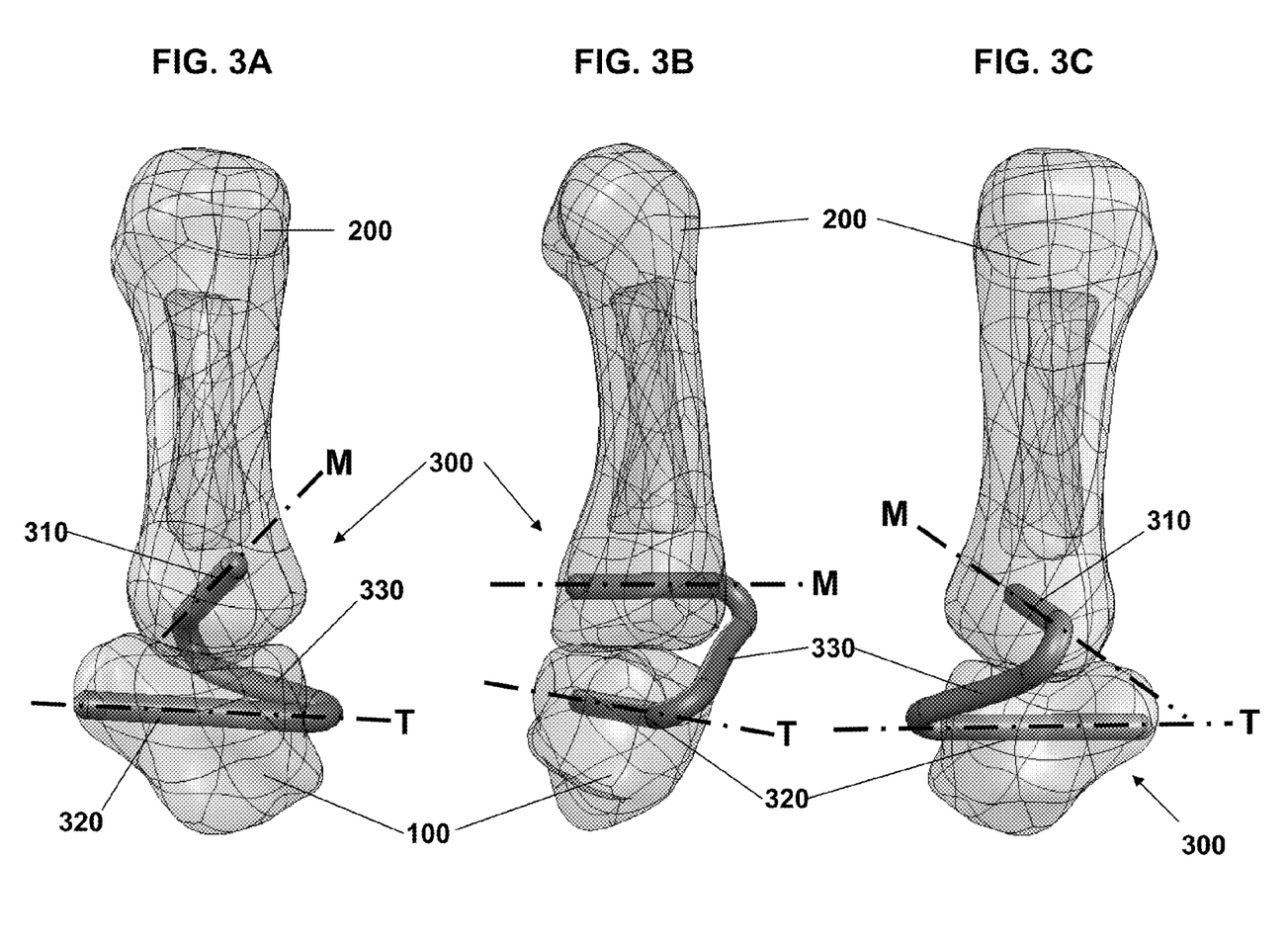
FIG. 3A-3C show perspective views from different viewpoints of one particular embodiment of a single part, internal joint stabilizer installed in a carpometacarpal joint.
Figures 4A, 4B:
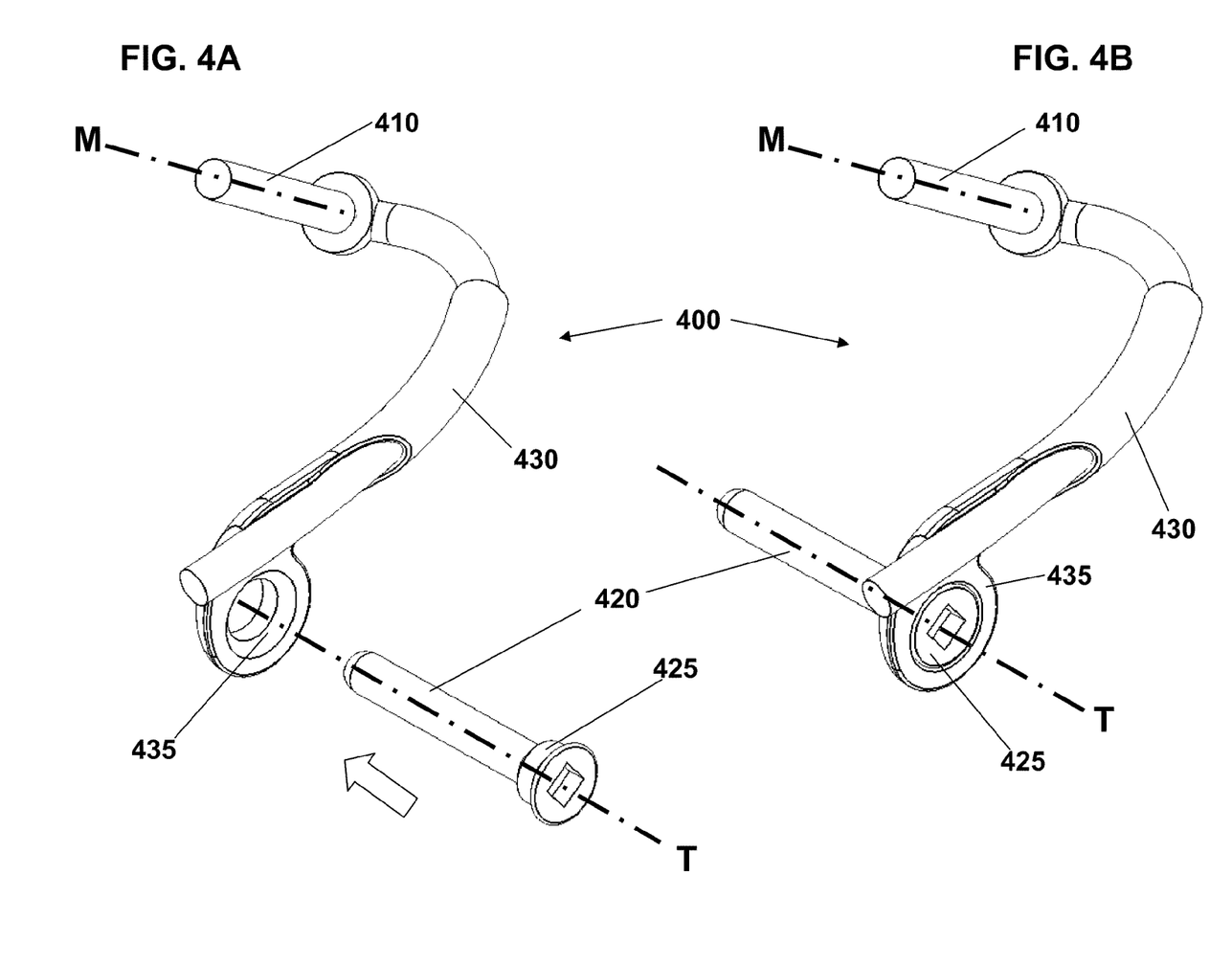
FIG. 4A is a partially exploded perspective view of one embodiment of a multi-part internal joint stabilizer for the carpometacarpal joint.
FIG. 4B is an assembled perspective view of the multi-part internal joint stabilizer of FIG. 4A.
Figures 4C, 4D:
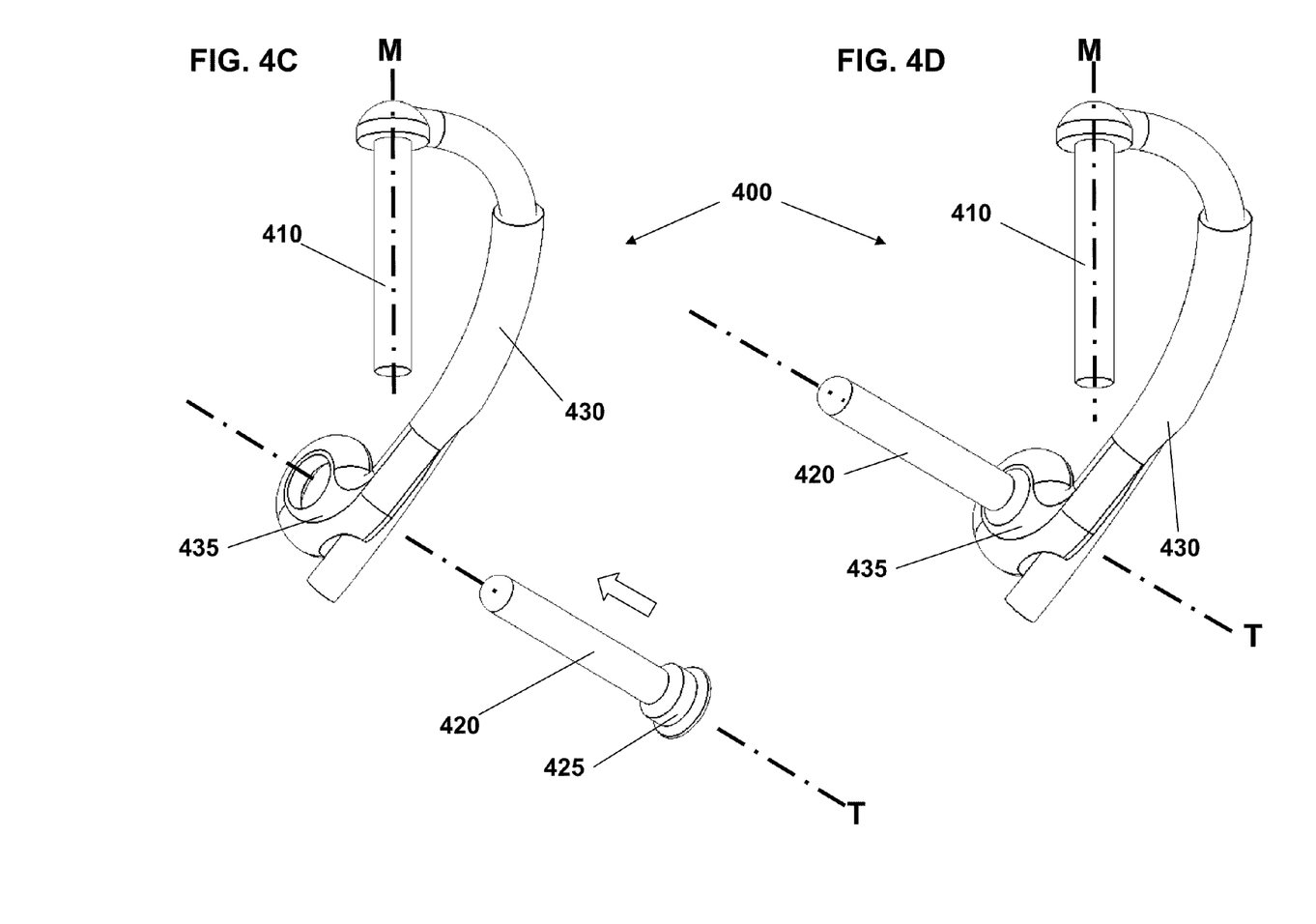
FIG. 4C is a perspective view of the partially exploded multi-part internal joint stabilizer of FIG. 4A, from a different viewpoint.
FIG. 4D is an assembled perspective view of the multi-part internal joint stabilizer of FIG. 4C.

As shown more particularly in FIGS. 3A-3C, the IJS 300 can be installed in the CMC joint formed by the first metacarpal 200 and the trapezium 100. As can be appreciated the axle portions 310, 320 of IJS 300 are aligned with first axis of rotation M in the first metacarpal 200 and second axis of rotation T in the trapezium 100, respectively. This allows the early movement of the joint through its natural range of motion, leading to a faster recovery.

The IJS 300 of the instant embodiment can be made of bio-compatible metal such as titanium, or a shape memory alloy such as nitinol, or, alternatively, of a bioabsorbable material such as PLA. In the case of metal, it could be removed at a later date, once the joint has healed. If made of reabsorbable material, the IJS 300 could permanently remain in the joint.

A single part IJS 300 for the CMC joint is desirable, because of its integral nature. However, it should be understood that an IJS made having one or more removable axles joinable by a body portion could be made. The use of such a multi-part IJS can provide even greater ease of installation in a joint, as will now be described in connection with FIGS. 4A-5B.

More particularly, in order to facilitate the placement of an IJS in a CMC or other joint, a multi-part IJS 400 for a multi-axis joint (such as, a CMC joint or other, similar joint), in accordance with another embodiment of the present invention, can be provided. Referring now to FIGS. 4A-4D therein is shown a multi-part IJS 400. The multi-part IJS 400 includes a first axle portion 410, a second axle portion 420 and a body portion 430, therebetween. The first axle portion 410 is adapted to be installed in the first metacarpal 200 in alignment with (i.e., collinear with) the first axis of rotation M. The second axle portion 420 is adapted to be installed in the trapezium 100, in alignment with (i.e., collinear with) the second axis of rotation T. In the present particular embodiment, the second axle portion 420 has a threaded head 425 at one end.

The body portion 430 of IJS 400 is geometrically adapted to allow the correct spatial alignment of first and second axle portions 410, 420, such that the alignment of the axles 410, 420, relative to the body portion 430, replicates the spatial alignment of first and second axis M, T. In one particular embodiment, the body portion 430 may be permanently attached to the first axle portion 410. In an alternate embodiment, the body portion 430 may be configured as a sliding sleeve that permits translational and/or rotational adjustment of the first axle portion 410 within the sleeve and, once adjusted, permanently affixed to first axle portion 410 by mechanical or other means, such as crimping. Furthermore, the body portion 430 includes a threaded eyelet 435 intended to receive the second axle portion 420, therethrough, and to torqueably engage the threaded head portion 425 of second axle portion 420.

Figure 5A:
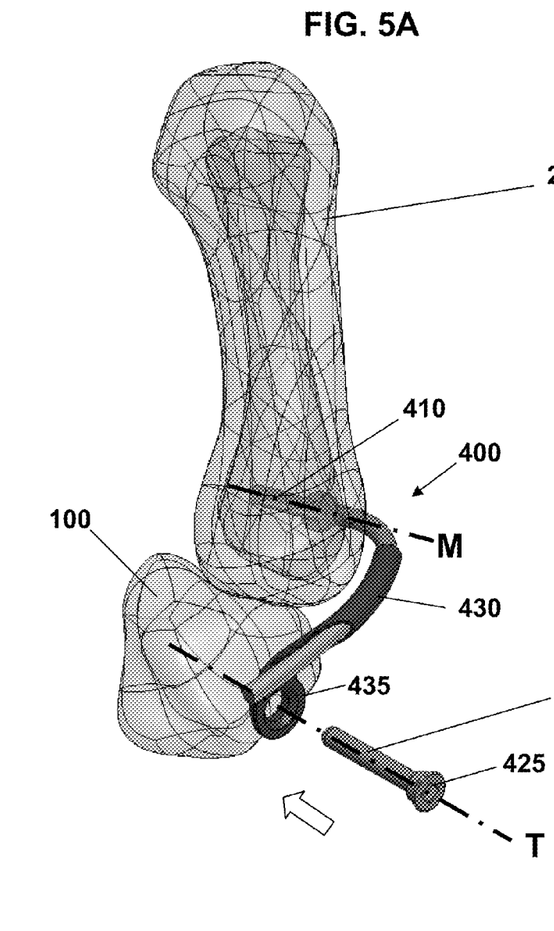
FIG. 5A is a partially exploded perspective view of the multi-part internal joint stabilizer of FIG. 4A, partially installed in a carpometacarpal joint.
Figure 5B:
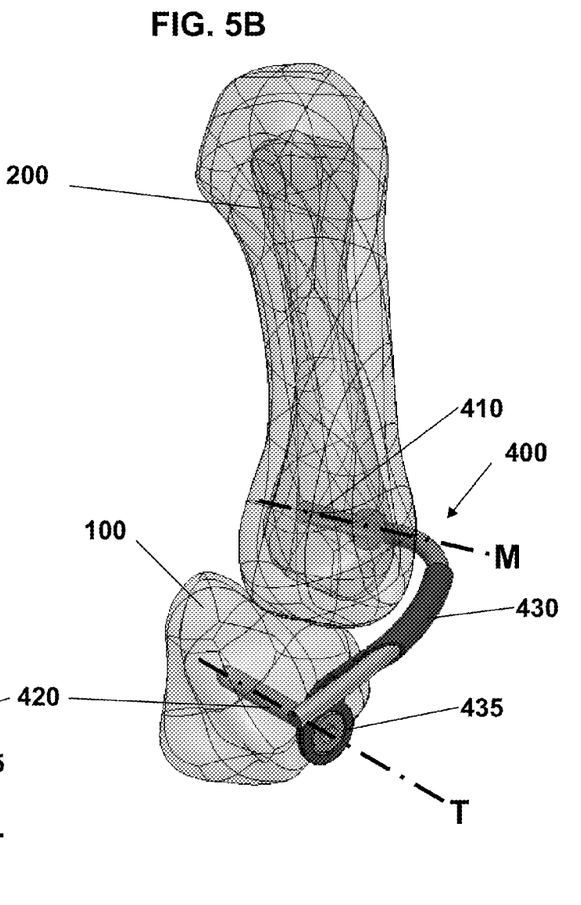
FIG. 5B is a perspective view of the multi-part internal joint stabilizer of FIG. 4A, fully installed in a carpometacarpal joint.

Referring now to FIGS. 5A-5B, the multi-part IJS 400 is shown in conjunction with the CMC joint between the first metacarpal 200 and the trapezium 100. In particular, FIG. 5A shows the multi-part IJS 400 having the first axle portion 410 installed into the first metacarpal 200 in alignment with first axis of rotation M, while second axle portion 420 is shown aligned with second axis of rotation T but not yet installed into the trapezium 100. FIG. 5B shows the fully installed multi-part IJS 400, after the first and second axle portions 410, 420 have been installed in the first metacarpal 200 and trapezium 100, respectively, in alignment with the natural, respective axes of rotation M, T. Note that, the full installation of the second axle portion 420 additionally requires the second axle portion to be passed through the hole 435 of the body portion, and the threaded head portion 425 of the second axle portion 420 has been matingly engaged with the threads on the threaded eyelet 435 of body portion 430.

As in the single part IJS embodiment 300, the multi-part IJS embodiment 400 can be made of a bio-compatible metal, such as titanium, or of a bioabsorbable material such as PLA. Alternatively, the different portions of multi-part IJS 400 may be selectively made of bio-compatible metal or of bioabsorbable material as desired.

The installation of IJS 300 and/or IJS 400 may be aided by the use of one or more axis locating tools and jigs (not shown) adapted to assist in locating the axis of rotation M in the first metacarpal and/or the axis of rotation T in the trapezium, and/or securing and manipulating the IJS parts during surgery.

To install the IJS 300, 400 in a multi-axis joint, the surgeon first locates the axes of rotation through the first and second bones of the joint. In the present example using the CMC joint, the surgeon locates the axes of rotation M of the first metacarpal 200 and T of the trapezium 100, with or without the aid of one or more axis locating tools (not shown). After locating the axes M and T, holes are drilled partially through the bones in alignment with those axes of rotation M, T. Thereafter, the first axle portion 310, 410 of the IJS 300, 400 is inserted into the pre-drilled hole of the first metacarpal bone 200. The body portion 330, 430 is then rotated around the M axis, to facilitate the placement of the second axle portion 320, 420. When installing the multi-part IJS 400, the body portion 430 is rotated around the M axis so that the eyelet 435 of the body portion is located over, and in alignment with, the pre-drilled hole in the trapezium 100. After which, the second axle portion 420 of the IJS 400 is inserted through the eyelet 435 and into the pre-drilled hole in the trapezium 100. Finally, the threaded head portion 425 of the second axle portion 420 is torqueably engaged with a mating thread of the threaded eyelet portion 435.

On occasion, the articular surfaces of one or more of the bones forming a multi-axis joint may be eroded or otherwise damaged. In those cases, it is sometimes necessary to install a prosthesis to replace the eroded or damaged articular surface before attempting to stabilize the multi-axis joint with an IJS, as described with the embodiments above.

Figure 6A:
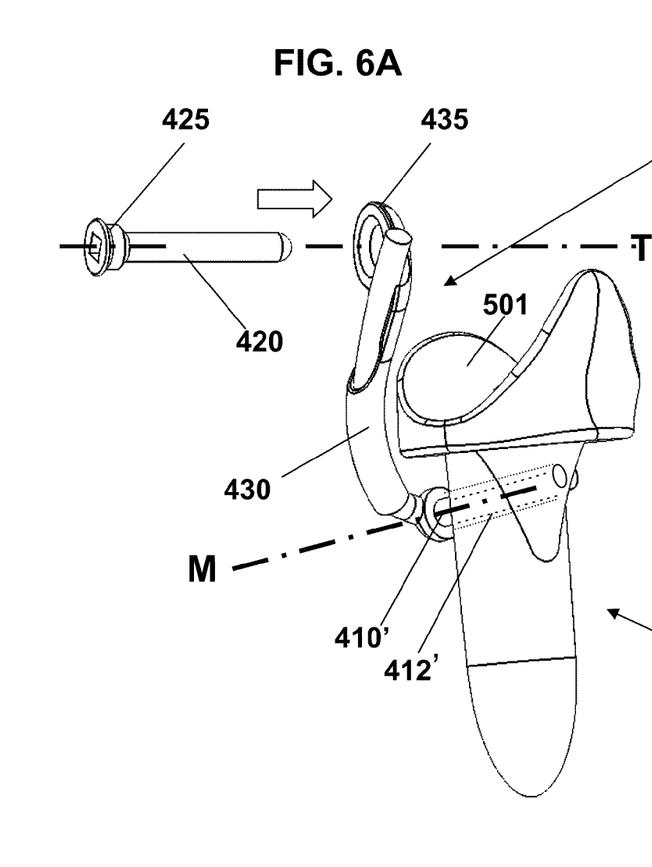
FIG. 6A is a perspective, partially exploded view of a multi-part internal joint stabilizer to be installed in conjunction with a prosthesis device, in accordance with another embodiment of the invention.
Figure 6B:
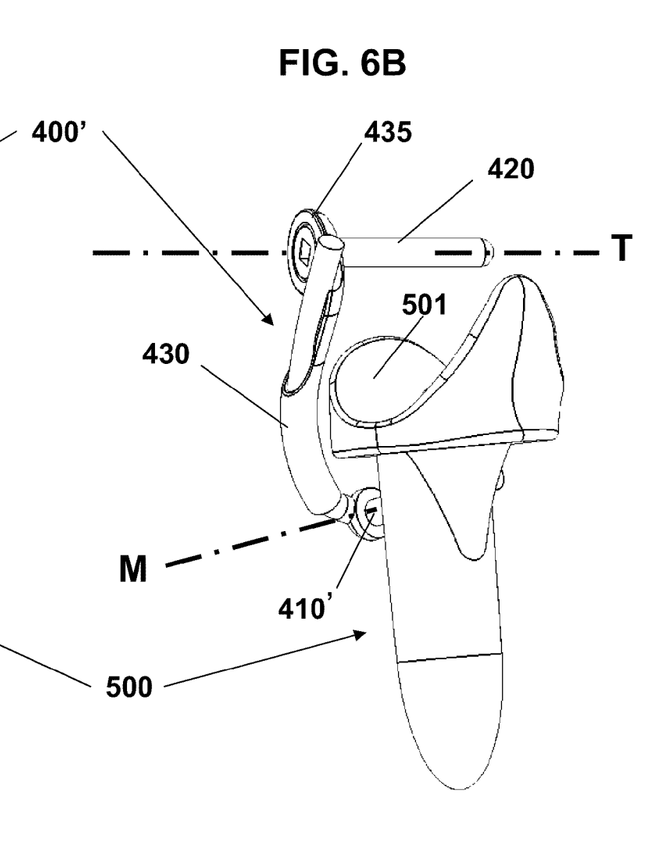
FIG. 6B is a perspective view of the assembled, multi-part internal joint stabilizer of FIG. 6A.
Figure 7:
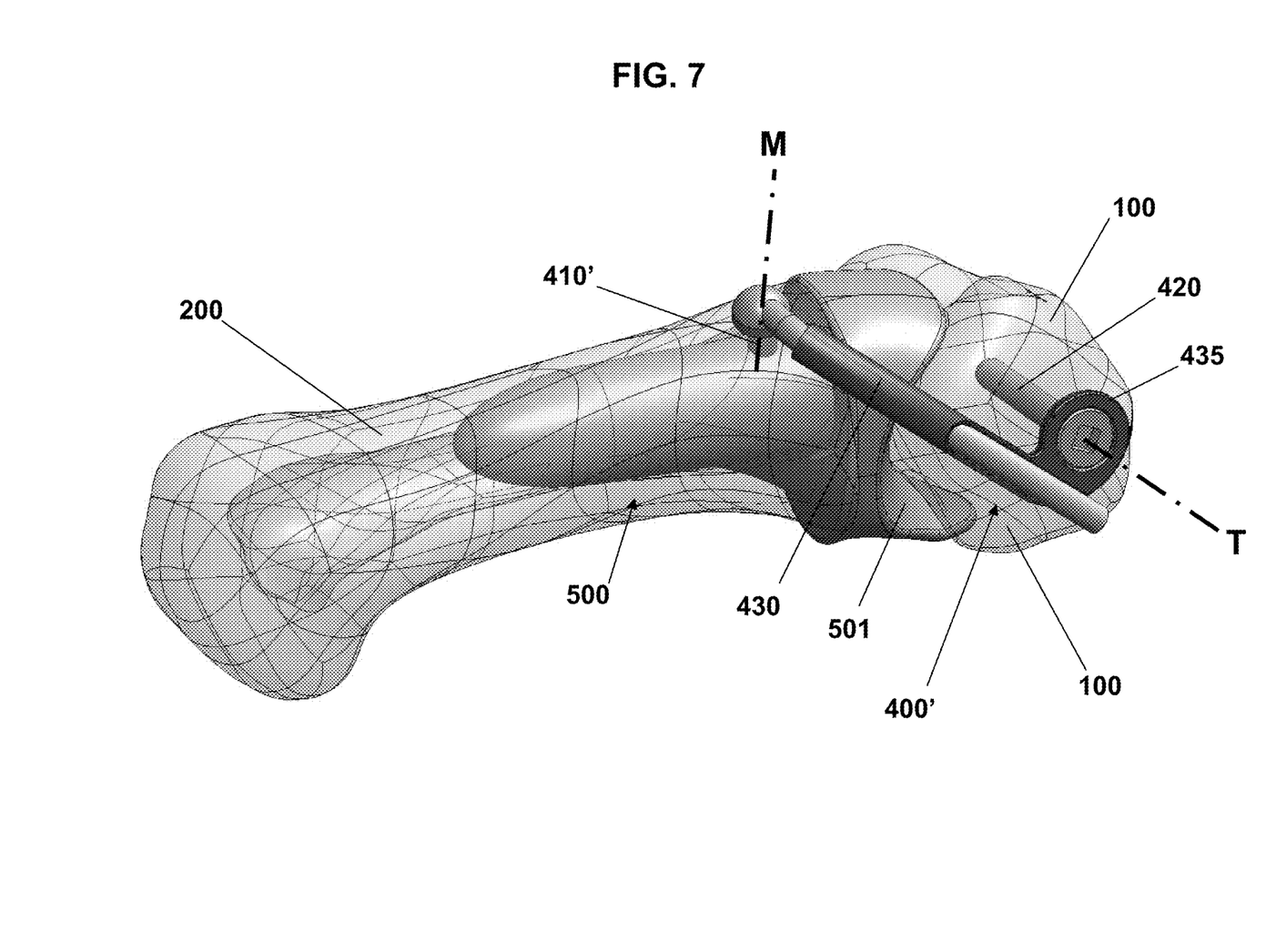
FIG. 7 is a perspective view of the multi-part internal joint stabilizer of FIG. 6A fully installed in a carpometacarpal joint.

Referring now to FIGS. 6A-7 there is shown a multi-part IJS 400' for use in a multi-axis joint, which is used in conjunction with a prosthesis 500. Although described herein in connection with the CMC joint and, more particularly, with a prosthesis for replacing the proximal metacarpal, it should be understood that the theory, devices and techniques described herein can be adapted for use with other bones of other multi-axis joints.

Referring back to FIGS. 6A-7, the prosthesis 500 is adapted to be inserted into the proximal medullary canal of the first metacarpal after removing that part of the bone that is eroded or damaged, including the saddle-shaped articular surface of the bone. The prosthesis 500 includes a saddle-shaped articular surface 501 that, upon installation of the prosthesis 500 in the bone, replaces the similarly shaped articular surface that was removed. As more clearly seen in FIG. 6A, prosthesis 500 is further adapted to include a channel or cavity 412', to receive a first axle portion 410' of IJS 400'.

The installation of IJS 400' in a multi-axis joint, in this example, the CMC joint, follows the same steps as described hereinabove in connection with the procedure for installing IJS 400, but with the additional prior steps of resecting the damaged proximal end of the first metacarpal 200 and inserting the prosthesis 500 into the exposed medullary canal of the first metacarpal 200.

Although described above in connection with the carpometacarpal joint, this is not meant to be limiting, as other IJS can be made in accordance with the description herein, but of different size or scale, so as to treat instability or dislocations of other multi-axis hinged joints, as desired. As such, although the invention is illustrated and described herein, various modifications and structural changes may be made therein without departing from the spirit of the invention and within the scope and range of equivalents of the claims.

What is claimed is:

1. An internal joint stabilizer for a joint having multiple axes of rotation, comprising:
    a first axle portion adapted to be installed in a first bone of the joint having a first axis of rotation;
    a second axle portion adapted to be installed in a second bone of the joint having a second axis of rotation;
    a body portion in communication with said first axle portion and said second axle portion, said body portion including a threaded eyelet for removably engaging a threaded head on the second axle;
    the body portion being configured to simultaneously hold the first axle collinear with the first axis of rotation and the second axle portion collinear with the second axis of rotation; and
    wherein the internal joint stabilizer is formed from a plurality of interlocking parts.

2. The internal joint stabilizer of claim 1, wherein the position of the first axle is at least one of rotationally or translationally adjustable relative to the body portion.

3. The internal joint stabilizer of claim 1, further including a prosthesis including an articular surface for replacing an articular surface of one of the first and second bones, the prosthesis including a hole therein for receiving one of the first and second axle portions.

4. The internal joint stabilizer of claim 1, wherein the first bone is a first metacarpal and the second bone is a trapezium.

5. A method of installing an internal joint stabilizer for a joint having multiple axes of rotation, comprising the steps of:
    providing an internal joint stabilizer including a first axle portion for fixation to a first bone of the joint, a second axle portion for fixation to a second bone of the joint, and a body portion in communication with the first axle portion and the second axle portion, the body portion configured to maintain a longitudinal axis of the first axle portion skew to a longitudinal axis of the second axle portion;
    drilling a first hole in a first bone of a joint in alignment with a first axis of rotation of the joint;
    drilling a second hole in a second bone of the joint in alignment with a second axis of rotation of the joint;
    inserting the first axle portion into the first hole in the first bone;
    inserting the second axle portion into the second hole in the second bone; and
    wherein the internal joint stabilizer is a multi-part internal joint stabilizer and the body portion includes a threaded eyelet matingly engageable with a threaded head of the second axle portion.

6. The method of claim 5, further comprising the steps of:
    after inserting the first axle portion into the first hole, rotating the body portion, without the second axle portion being attached, to align the eyelet with the second hole; and
    after the rotating step, passing the body of the second axle portion through the eyelet and into the second hole and matingly engaging the threaded head of the second axle portion with the threaded eyelet.

7. The method of claim 5, wherein the first bone is a first metacarpal and the second bone is a trapezium.

* * * * *